United States Patent
Song

(10) Patent No.: US 9,721,186 B2
(45) Date of Patent: Aug. 1, 2017

(54) GLOBAL SIGNATURES FOR LARGE-SCALE IMAGE RECOGNITION

(71) Applicant: Nant Holdings IP, LLC, Culver City, CA (US)

(72) Inventor: Bing Song, La Canada, CA (US)

(73) Assignee: Nant Holdings IP, LLC, Culver City, CA (US)

(*) Notice: Subject to any disclaimer, the term of this patent is extended or adjusted under 35 U.S.C. 154(b) by 0 days.

(21) Appl. No.: 15/063,271

(22) Filed: Mar. 7, 2016

(65) Prior Publication Data

US 2016/0259816 A1     Sep. 8, 2016

Related U.S. Application Data

(60) Provisional application No. 62/128,959, filed on Mar. 5, 2015.

(51) Int. Cl.
*G06K 9/54* (2006.01)
*G06K 9/60* (2006.01)
(Continued)

(52) U.S. Cl.
CPC ......... *G06K 9/6201* (2013.01); *G06K 9/4676* (2013.01); *G06K 9/6255* (2013.01)

(58) Field of Classification Search
None
See application file for complete search history.

(56) References Cited

U.S. PATENT DOCUMENTS 6,711,293 B1    3/2004 Lowe
7,657,100 B2    2/2010 Gokturk et al.
(Continued)

FOREIGN PATENT DOCUMENTS

CN    102063472 A    5/2011
EP    2 383 680 A1   11/2011
(Continued)

OTHER PUBLICATIONS

Douze et al., "Combining attributes and Fisher vectors for efficient image retrieval", CVPR 2011—IEEE Conference on Computer Vision & Pattern Recognition, Jun. 2011, IEEE, 9 pages.
(Continued)

*Primary Examiner* — Feng Niu
(74) *Attorney, Agent, or Firm* — Mauriel Kapouytian Woods LLP; Andrew A. Noble; Michael Mauriel

(57) ABSTRACT

Techniques are provided that include obtaining a vocabulary including a set of content indices that reference corresponding cells in a descriptor space based on an input set of descriptors. A plurality of local features of an image are identified based on the vocabulary, the local features being represented by a plurality of local descriptors. An associated visual word in the vocabulary is determined for each of the plurality of local descriptors. A plurality of global signatures for the image are generated based on the associated visual words, wherein some of the plurality of global signatures are generated using local descriptors corresponding to different cropped versions of the image, two or more of the different cropped versions of the image being centered at a same pixel location of the image, and an image recognition search is facilitated using the plurality of global signatures to search a document image dataset.

30 Claims, 6 Drawing Sheets

(51) Int. Cl.
G06K 9/62 (2006.01)
G06K 9/46 (2006.01)

(56) References Cited

U.S. PATENT DOCUMENTS

| | | | |
|---|---|---|---|
| 7,680,341 | B2 | 3/2010 | Perronnin |
| 7,783,135 | B2 | 8/2010 | Gokturk et al. |
| 8,139,900 | B2 | 3/2012 | Gokturk et al. |
| 8,489,585 | B2 | 7/2013 | Larlus et al. |
| 8,630,513 | B2 | 1/2014 | Gokturk et al. |
| 8,712,862 | B2 | 4/2014 | Gokturk et al. |
| 8,732,025 | B2 | 5/2014 | Gokturk et al. |
| 8,768,049 | B2 | 7/2014 | Wang et al. |
| 8,768,313 | B2 | 7/2014 | Rodriguez |
| 8,879,796 | B2 * | 11/2014 | Rodriguez Serrano ............ G06K 9/325 382/105 |
| 8,983,201 | B2 * | 3/2015 | Cai .................... G06K 9/4676 382/195 |
| 9,547,807 | B2 * | 1/2017 | Vidal Calleja ....... G06K 9/4676 |
| 2007/0217676 | A1 | 9/2007 | Grauman et al. |
| 2007/0260639 | A1 | 11/2007 | Tobin et al. |
| 2008/0301133 | A1 | 12/2008 | Brown et al. |
| 2009/0297048 | A1 | 12/2009 | Slotine et al. |
| 2011/0013556 | A1 | 1/2011 | Molnar et al. |
| 2012/0082378 | A1 | 4/2012 | Peters et al. |
| 2013/0129223 | A1 | 5/2013 | Takacs et al. |
| 2013/0202213 | A1 | 8/2013 | Adamek et al. |
| 2014/0015855 | A1 | 1/2014 | Denney et al. |
| 2014/0019489 | A1 | 1/2014 | Wang et al. |
| 2014/0056520 | A1 * | 2/2014 | Rodriguez Serrano ............ G06K 9/325 382/174 |
| 2014/0254923 | A1 * | 9/2014 | Vidal Calleja ....... G06K 9/4676 382/159 |
| 2014/0369626 | A1 | 12/2014 | Gokturk et al. |
| 2015/0011194 | A1 | 1/2015 | Rodriguez |
| 2015/0262036 | A1 | 9/2015 | Song et al. |
| 2016/0259815 | A1 | 9/2016 | Song et al. |

FOREIGN PATENT DOCUMENTS

| | | |
|---|---|---|
| WO | WO 2012/156774 A1 | 11/2012 |
| WO | WO 2013/056315 A1 | 4/2013 |

OTHER PUBLICATIONS

Zobel et al., "Inverted Files for Text Search Engines", ACM Computing Surveys, Jul. 2006, vol. 38, No. 2, Article 6, 56 pages.

Jegou et al., "Triangulation embedding and democratic aggregation for image search", CVPR—International Conference on Computer Vision and Pattern Recognition (2014), 12 pages.

Jegou et al., "Aggregating local descriptors into a compact image representation", 2010 IEEE Conference on Computer Vision and Pattern Recognition (CVPR), 8 pages.

Arandjelovic et al., "Three things everyone should know to improve object retrieval", CVPR '12 Proceedings of the 2012 IEEE Conference on Computer Vision and Pattern Recognition (CVPR), 8 pages.

Spyromitros-Xioufis et al., "A Comprehensive Study over VLAD and Product Quantization in Large-scale Image Retrieval", IEEE Transactions on Multimedia, Oct. 2014, vol. 16, Issue 6, 16 pages.

Arandjelovic et al., "All about VLAD", IEEE Conference on Computer Vision and Pattern Recognition, 2013, 8 pages.

Jegou et al., "Product quantization for nearest neighbor search", IEEE Transactions on Pattern Analysis and Machine Intelligence, Jan. 2011, vol. 33, Issue 1, 14 pages.

Lowe, "Distinctive Image Features from Scale-Invariant Keypoints", International Journal of Computer Vision, Nov. 2004, vol. 60, Issue 2, 28 pages.

Razavian et al., "Visual Instance Retrieval with Deep Convolutional Network", Computer Science—Computer Vision and Pattern Recognition, Dec. 2014, 8 pages.

Sivic et al., "Video Google: A Text Retrieval Approach to Object Matching in Videos", Proceedings of the Ninth IEEE International Conference on Computer Vision (ICCV), 2003, vol. 2, 8 pages.

Winn et al., "Object Categorization by Learned Universal Visual Dictionary", ICCV '05 Proceedings of the Tenth IEEE International Conference on Computer Vision, vol. 2, 8 pages.

Cummins et al., "Probabilistic Appearance Based Navigation and Loop Closing", 2007 IEEE International Conference on Robotics and Automation, 7 pages.

Jegou et al., "Searching in One Billion Vectors: Re-Rank With Source Coding", ICASSP 2011—International Conference on Acoustics, Speech and Signal Processing, May 2011, 4 pages.

Turcot et al., "Better matching with fewer features: The selection of useful features in large database recognition problems", 2009 IEEE 12th International Conference on Computer Vision Workshops (ICCV Workshops), 8 pages.

Girod et al., "Mobile Visual Search", IEEE Signal Processing Magazine, Jul. 2011, vol. 28, Issue 4, pp. 61-76.

Mejdoub et al., "Embedded Lattices Tree: An Efficient Indexing Scheme for Content Based Retrieval on Image Databases", Journal of Visual Communication and Image Representation, Feb. 2009, vol. 20, Issue 2, pp. 145-156.

Mikulik et al., "Learning a Fine Vocabulary", ECCV'10 Proceedings of the 11th European conference on computer vision conference on Computer vision: Part III, 14 pages.

Mikulik et al., "Learning Vocabularies Over a Fine Quantization", International Journal of Computer Vision, May 2013, vol. 103, Issue 1, 13 pages.

Morioka et al., "Building Compact Local Pairwise Codebook with Joint Feature Space Clustering", Computer Vision—ECCV 2010, vol. 6311, 14 pages.

Nister et al., "Scalable Recognition with a Vocabulary Tree", 2006 IEEE Computer Society Conference on Computer Vision and Pattern Recognition, vol. 2, 8 pages.

Philbin et al., "Object Retrieval with Large Vocabularies and Fast Spatial Matching", 2007 IEEE Conference on Computer Vision and Pattern Recognition (CVPR '07), 8 pages.

Philbin, "Scalable Object Retrieval in Very Large Image Collections", PhD thesis from University of Oxford, 2010, 181 pages.

Silpa-Anan et al., "Optimised KD-Trees for Fast Image Descriptor Matching", IEEE Conference on Computer Vision and Pattern Recognition (CVPR 2008), 8 pages.

International Search Report and Written Opinion issued in International Application No. PCT/US2015/015958 dated Aug. 19, 2015, 14 pages.

* cited by examiner

GLOBAL SIGNATURES FOR LARGE-SCALE IMAGE RECOGNITION

CROSS REFERENCE TO RELATED APPLICATIONS

This application claims the benefit of U.S. Provisional Application No. 62/128,959, filed Mar. 5, 2015, the entire content of which is hereby incorporated herein by reference.

TECHNICAL FIELD

This disclosure relates generally to object instance recognition, and more specifically to object instance recognition techniques for digital image recognition searches.

BACKGROUND

Many attempts have been made to improve the scope, accuracy, compactness, efficiency and speed of image recognition and retrieval technologies that may be applied, for example, to implement large-scale digital image recognition searches. One focus of such attempts has been feature detection and description. At the most basic level, descriptors provide a means to characterize, summarize and index distinguishing features of an image (e.g., shapes, objects, etc.) for purposes of image recognition, search and retrieval. There are various methods for generating descriptors that represent the local features of an image. For example, the scale-invariant feature transform (SIFT), such as described in U.S. Pat. No. 6,711,293 to Lowe, is a currently popular image recognition algorithm used to detect and describe local features of images.

A global signature is a full image descriptor. One example of a global signature is a vector of locally aggregated descriptors (VLAD) built from local descriptors. In some instances, a global signature may be compressed or reduced in size (e.g., in relation to a sum of the local descriptors for an image) by further techniques to be a more compact method of describing images relative to large amounts of local descriptors. For example, one current technique for compressing global signatures is principal components analysis (PCA). Notably, the compression of global signatures can reduce the memory requirements necessary to practically operate an image recognition system.

SUMMARY

Local descriptors (e.g., SIFT local descriptors) are a relatively accurate way to characterize, summarize and index distinguishing features of an image. In general, local descriptor accuracy is achieved because each image can be associated with several hundred, or even several thousand, local descriptors. However, a significant problem with using large numbers of local descriptors per image for large-scale image recognition (e.g., an image dataset of 10 million or more images) is the memory and processing power required to store and search local descriptors for a large image dataset. As a result, in many cases large-scale image recognition using only local descriptors is impractical.

Global signatures have been seen as a solution to reduce the memory requirements for large-scale image recognition. However, the advantages of using global signatures are typically offset by concerns about a potential loss in accuracy for image recognition search results. Of particular concern is the inherent loss of information about various local features of an image caused by summarizing and compressing large numbers of local descriptors (e.g., the hundreds or thousands of local descriptors). For example, in some cases global signatures for a group of images can be relatively similar, and practically indistinguishable, if the images include the same types of objects. In other cases, global signatures may obscure critical image recognition factors, such as the presence of multiple objects in images, the scale of objects depicted in images, etc. Therefore, the effectiveness of image recognition using theoretically efficient global signatures (in terms of processing speed, memory requirements and other factors) is often counterbalanced by the accuracy requirements for implementing a practical and reliable large-scale image recognition system. Until now, the use of global signatures for large-scale image recognition systems has been limited due to these concerns.

Systems, methods and articles of manufacture related to global signatures for large-scale image recognition are described herein. The various embodiments can allow for a large-scale image recognition system, comprising multiple servers and user devices, to be made more efficient for processing image recognition queries by using global signature information. In one embodiment, a vocabulary, including a set of content indices that reference corresponding cells in a descriptor space based on an input set of descriptors, is obtained. A plurality of local features of an image are identified based on the vocabulary, the local features being represented by a plurality of local descriptors. The plurality of local descriptors may be one of scale-invariant feature transform (SIFT) descriptors, Fast Retina Keypoint (FREAK) descriptors, Histograms of Oriented Gradient (HOG) descriptors, Speeded Up Robust Features (SURF) descriptors, DAISY descriptors, Binary Robust Invariant Scalable Keypoints (BRISK) descriptors, FAST descriptors, Binary Robust Independent Elementary Features (BRIEF) descriptors, Harris Corners descriptors, Edges descriptors, Gradient Location and Orientation Histogram (GLOH) descriptors, Electrooculography (EOG) descriptors or Transform Invariant Low-rank Textures (TILT) descriptors. The image may be a query image. An associated visual word in the vocabulary is determined for each of the plurality of local descriptors. A plurality of global signatures are generated for the image based on the associated visual words, wherein some of the plurality of global signatures are generated using local descriptors corresponding to different cropped versions of the image, two or more of the different cropped versions of the image being centered at a same pixel location of the image, and an image recognition search is facilitated using the plurality of global signatures to search a document image database. The plurality of global signatures may be vector of locally aggregated descriptors (VLAD) global signatures.

In some embodiments, the plurality of global signatures may include at least four global signatures. A one of the plurality of global signatures generated using local descriptors corresponding to a cropped version of the image may be centered at a different pixel location of the image with respect to another one of the plurality of global signatures. In some embodiments, some of the plurality of global signatures may be generated using local descriptors corresponding to an uncropped version of the image.

Various objects, features, aspects and advantages of the inventive subject matter will become more apparent from the following specification, along with the accompanying drawings in which like numerals represent like components.

Figure 1A:
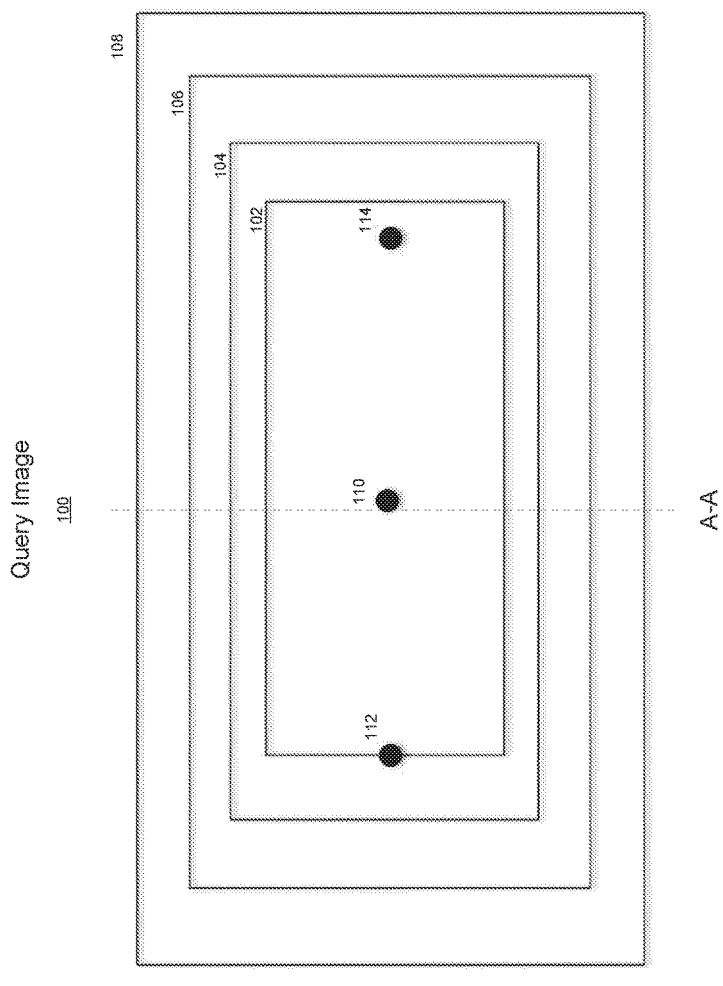
FIG. 1A illustrates an example of different cropped versions of an image in accordance with an embodiment.

While the invention is described with reference to the above drawings, the drawings are intended to be illustrative, and other embodiments are consistent with the spirit, and within the scope, of the invention.

SPECIFICATION

The various embodiments now will be described more fully hereinafter with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator, and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on".

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term "comprising" means to have as parts or members, or to be those parts or members. As used herein, the transitional term "comprising" is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The focus of the disclosed inventive subject matter is to enable construction or configuration of a computing device to operate on vast quantities of digital data, beyond the capabilities of a human. Although, in some embodiments, the digital data represents images, it should be appreciated that the digital data is a representation of one or more digital models of images, not necessarily the images themselves. By instantiation of such digital models in the memory of the computing devices, the computing devices are able to manage the digital data or models in a manner that could provide utility to a user of the computing device that the user would lack without such a tool.

One should appreciate that the disclosed techniques provide many advantageous technical effects including improving the scope, accuracy, compactness, efficiency and speed of computer-based image recognition and retrieval technologies. It should also be appreciated that the following specification is not intended as an extensive overview, and as such, concepts may be simplified in the interests of clarity and brevity.

In accordance with the various embodiments, object instance retrieval, referred to herein in the context of image retrieval and/or image recognition, involves systems and methods of feature detection for an image dataset (referred to herein individually as "images" or "document images") in response to a given query image. Image recognition is made possible through the use of descriptors that characterize, summarize and index distinguishing features of an image. Large-scale image recognition can involve multiple servers running in parallel and image datasets of 10 million or more images per server (relative to image datasets of about 1 million images per server for medium-scale image recognition). However, due to the storage requirements for the descriptors that correspond to large image datasets, there is often a tradeoff between the memory footprint of an image descriptor and image retrieval performance as measured by, for example, mean average precision (mAP). Therefore, compact image descriptors are preferable to perform image recognition on a large scale.

Local descriptors are vectors that correspond to one or more distinguishable local features of an image (e.g., shapes, objects, etc.). There are various methods for detecting image features and generating local descriptors. For example, the scale-invariant feature transform (SIFT) is a currently popular image recognition algorithm used to detect and describe local features of images. SIFT descriptors are 128-dimensions in order to be highly distinctive (i.e., distinguishable for matching purposes) and at least partially tolerant to variations such as illumination, three-dimensional (3D) viewpoint, etc. For example, one reference related to generating SIFT descriptors is D. Lowe, "Distinctive Image Features from Scale-Invariant Keypoints", International Journal of Computer Vision 60 (2), pages 91-110 (2004). In addition to SIFT descriptors, other alternative local descriptors include Fast Retina Keypoint (FREAK) descriptors, Histograms of Oriented Gradient (HOG) descriptors, Speeded Up Robust Features (SURF) descriptors, DAISY descriptors, Binary Robust Invariant Scalable Keypoints (BRISK) descriptors, FAST descriptors, Binary Robust Independent Elementary Features (BRIEF) descriptors, Harris Corners descriptors, Edges descriptors, Gradient Location and Orientation Histogram (GLOH) descriptors, Electrooculography (EOG) descriptors and Transform Invariant Low-rank Textures (TILT) descriptors. Typically, each image of an image dataset may include hundreds or thousands of local features represented by local descriptors. Therefore, practical system constraints will often require means to both compress the amount of descriptors used to describe an image dataset, and to reduce in size the memory required to store the information contained in local descriptors.

A global signature is a full image descriptor that can represent an entire image or a cropped version of an image, rather than merely an object that an image contains. For example, Vector of Locally Aggregated Descriptors (VLAD) global signatures are one type of global signature used in the embodiments herein to represent entire images. In addition to VLAD signatures, other types of global image signatures include, for example, GIST signatures and Deep Learning signatures.

VLAD global signatures are compact, fixed-length vectors built from local descriptors. Ideally, if two images contain the same object, a distance measurement (e.g., a Hamming distance) between VLAD signatures representing the two images should be relatively small compared to a distance measurement between VLAD signatures representing images that do not contain the same object. In general, VLAD signatures (also referred to herein as "VLAD global signatures") are considered to be low-dimensional, in terms of bytes per image. As a result, it has been shown that VLAD signatures corresponding to large image datasets can be made to fit into a main memory device (e.g., a client device main memory or a server main memory). It should be noted that the term "signature" is used throughout this specification to describe descriptors that are "global" in nature, including VLAD signatures that correspond to an entire image or cropped versions of an image. Although the terms global signature and global descriptor should be considered to be interchangeable, the term global signature is used herein to distinguish such global feature descriptors from local descriptors, which correspond to local features.

A VLAD global signature may be constructed by extracting local features from an image that are described using local descriptors, such as 128-dimensional SIFT local descriptors. The image is then divided into k cluster centers (e.g., k may equal 64, 256 or another number), and each local descriptor of the image is assigned to a closest one of the k cluster centers. Then for each of the k cluster centers, the local descriptors are vector quantized by recording the residuals (differences) between each of the local descriptor vectors and the cluster centers to which they are assigned. The sums of the k residuals for each of the cluster centers are concatenated into a single (k*128 dimensional) VLAD signature. Typically, the VLAD signature is then compressed to reduce the number of dimensions by using, for example, a Principal Components Analysis (PCA) projection matrix. For example, applying a PCA projection matrix may reduce the number of dimensions of the VLAD signature by a factor of 100 or more (e.g., from k*128 dimensions to 64 dimensions).

Multiple spatial global signatures (including the "multiple VLAD signatures" referred to herein) may be determined for an image. For example, VLAD signatures that are focused around different cropped versions of an image can enable a recognition search for objects that are not centered in an image or only extend over a relatively small portion of an image (e.g., objects that cover less than a majority portion of a model/query image or objects that happen to be off-center in a typically centered model/query image), without having to revert to the use of local descriptors. Multiple VLAD signatures have been shown to improve image retrieval performance for small objects (i.e., objects that cover a relatively small portion of an image). One skilled in the art will appreciate that various techniques are possible for generating and compressing multiple VLAD signatures, including techniques in the areas of vocabulary adaptation and intra-normalization. For example, one reference related to generating and compressing multiple VLAD signatures is R. Arandjelovic and A. Zisserman, "All about VLAD", CVPR '13 Proceedings of the 2013 IEEE Conference on Computer Vision and Pattern Recognition, pages 1578-1585 (2013). Moreover, as mentioned above, other methods for generating global signatures are possible (e.g., methods for generating Deep Learning signatures) and one skilled in the art will further appreciate that the multiple global signatures described herein may be generated based on those methods. For example, one reference related to generating global signatures without using local descriptors is A. Razavian, J. Sullivan, A. Maki and S. Carlsson, "Visual Instance Retrieval with Deep Convolutional Network", arXiv preprint arXiv:1412.6574 (2014). As such, the examples for generating and compressing global signatures disclosed herein, while exemplary, should not be construed as being limited to the means explicitly disclosed.

FIG. 1A illustrates an example of different cropped versions of an image in accordance with an embodiment. In FIG. 1A, a plurality of cropped versions of image 100 are shown, and a plurality of VLAD global signatures may extracted that correspond to the different cropped versions of the image. For example, pixel location 110 may be the basis for a VLAD signature corresponding to all of image 100, denoted by box 108, as well as VLAD signatures corresponding to different cropped versions of image 100, such as cropped versions of image 100 denoted by boxes 102, 104 and 106. For example, generating a VLAD signature for a cropping of image 100 around pixel location 110 can include extracting local features represented by a plurality of local descriptors, such as 128-dimensional SIFT local descriptors, from within box 104. Box 104 is then divided into k cluster centers (e.g., k may equal 64 or 256), and each local descriptor within box 104 is assigned to a closest one of the k cluster centers. Then for each of the k cluster centers, the local descriptors are vector quantized by recording the residuals between each of the local descriptor vectors and the cluster centers to which they are assigned. The sums of the k residuals (or visual words) for each of the cluster centers are concatenated into a single (k*128 dimensional) VLAD signature for the image within box 104, which may then be compressed by using, for example, PCA (e.g., from k*128 dimensional to 64 dimensions).

Although image 100 may be a model/query image intended to be centered around a desired object of interest (e.g., the desired object of interest may be related to an object for sale on an e-commerce website), in certain instances, the desired object of interest may be located at an off-center location within image 100. As such, in another example, pixel location 112 may be used as a center point for a VLAD signature that corresponds to a cropped version of image 100 that includes the portion of the image to the left of linear segment A-A. Therefore, generating a VLAD signature would include extracting local features represented by a plurality of local descriptors, such as 128-dimensional SIFT local descriptors, only to the left of linear segment A-A. Likewise, a VLAD signature centered at pixel location 114 would correspond to a cropped version of image 100 that includes the portion of the image to the right of linear segment A-A, and generating the VLAD signature would include extracting local features represented by the plurality of local descriptors only to the right of linear segment A-A. While the cropped versions of image 100 shown in FIG. 1A would yield a total of 12 VLAD signatures (i.e., VLAD signatures for four different cropped versions of the image 102, 104, 106, 108 centered around three pixel locations 110, 112, 114), more or fewer VLAD signatures may be extracted from an image. In various embodiments, the global descriptor-based image recognition systems and methods described below contemplate using a single global (e.g., VLAD) signature to describe document images of an image dataset, and at least four global (e.g., VLAD) signatures to describe a query image. While a desirable number of global signatures for both document images and query images may depend on any combination of memory footprint constraints and recognition performance considerations, in general, only the query image will require multiple VLAD signatures (e.g., to capture objects of interest located at an off-center image location) because objects of interest will typically be centered in the document images of an image dataset.

Figure 1B:
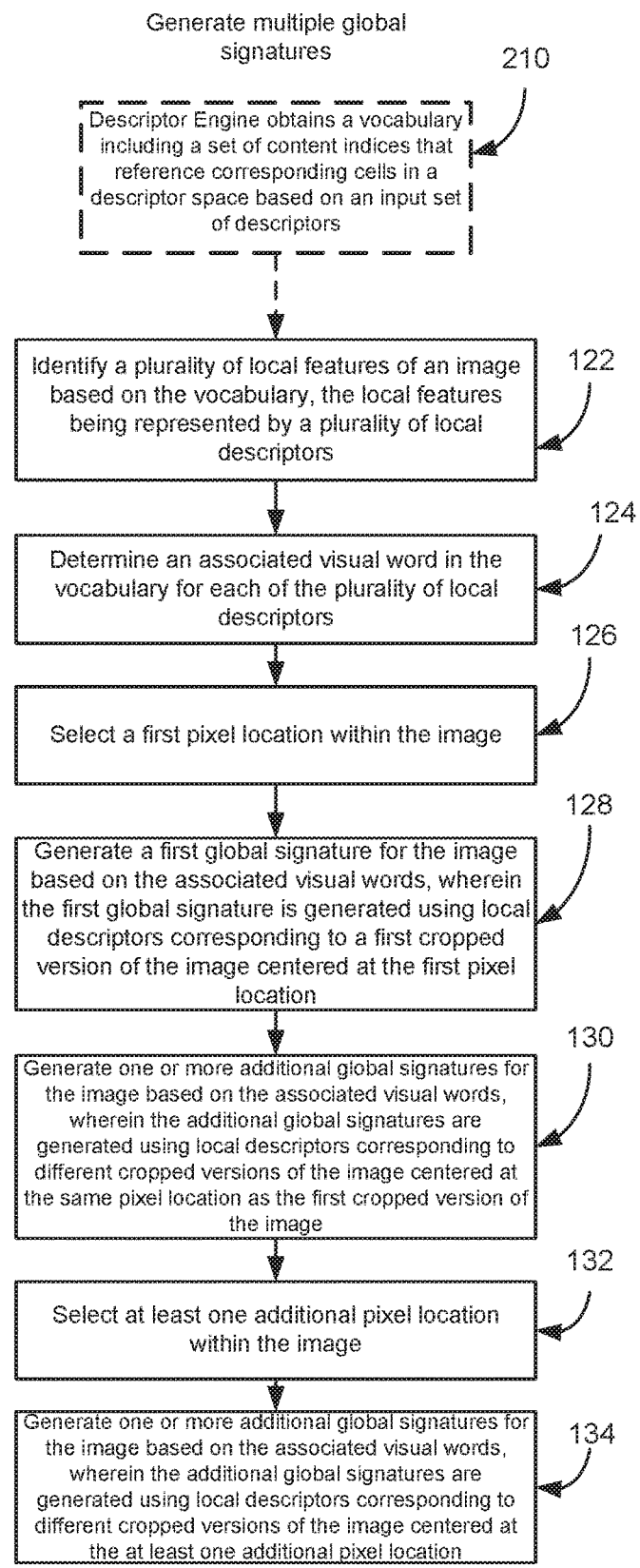
FIG. 1B illustrates a flow diagram of example operations for generating a plurality of global signatures for an image in accordance with an embodiment.

FIG. 1B illustrates a flow diagram of example operations for generating a plurality of global signatures for an image in accordance with an embodiment. In diagram 120, a descriptor engine (e.g., descriptor engine 210 in FIG. 2) obtains a vocabulary including a set of content indices that reference corresponding cells in a descriptor space based on an input set of descriptors. At step 122, a plurality of local features represented by a plurality of local descriptors are identified for an image, e.g., image 100, based on the vocabulary. In some embodiments, the plurality of local descriptors may be SIFT descriptors. In other embodiments, the plurality of local descriptors may be one of FREAK descriptors, HOG descriptors, SURF descriptors, DAISY descriptors, BRISK descriptors, FAST descriptors, BRIEF descriptors, Harris Corners descriptors, Edges descriptors, GLOH descriptors, EOG descriptors or TILT descriptors. At step 124, an associated visual word in the vocabulary is determined for each of the plurality of local descriptors. For example, a dictionary may be used to associate local descriptors with visual words. The dictionary may be a VLAD dictionary in which a plurality of visual words are based on descriptors determined from a training sample of model images.

At step 126, a first pixel location within the image is selected for generating a global signature. For example, the first pixel location may be a pixel location that corresponds to a center point of an image, such as pixel location 110 of image 100. At step 128, a first global signature (e.g., a VLAD signature) is generated for the image based on the associated visual words, wherein the first global signature is generated using local descriptors corresponding to a first cropped version of the image centered at the first pixel location within the image, e.g., cropped version 102 of image 100 shown in FIG. 1A. At step 130, one or more additional global signatures are generated for the image based on the associated visual words. In an embodiment, the additional global signatures are generated using local descriptors corresponding to different cropped versions of the image centered at the same pixel location as the first cropped version of the image. For example, the additional global signatures may be VLAD signatures for the cropped versions 104, 106 and 108 of image 100, as shown in FIG. 1A.

At step 132, at least one additional pixel location within image 100 is selected for generating a global signature. For example, the at least one additional pixel location may include pixel locations 112 and 114 of image 100. At step 134, one or more additional global signatures are generated for the image based on the associated visual words, wherein the additional global signatures are generated using local descriptors corresponding to different cropped versions of the image centered at the at least one additional pixel location. For example, pixel location 112 may be used as a center point for a VLAD signature that corresponds to a cropped version of image 100 that includes the portion of the image to the left of linear segment A-A. Therefore, generating a VLAD signature would include extracting local features represented by a plurality of local descriptors, such as 128-dimensional SIFT local descriptors, only to the left of linear segment A-A. Likewise, a VLAD signature centered at pixel location 114 would correspond to a cropped version of image 100 that includes the portion of the image to the right of linear segment A-A, and generating the VLAD signature would include extracting local features represented by the plurality of local descriptors only to the right of linear segment A-A.

The plurality of global signatures will preferably include at least four global signatures, but more or fewer global signatures may be generated. Further, in some embodiments one of the plurality of global signatures may be generated using local descriptors corresponding to an uncropped version of the image. As a result of generating a plurality of global signatures for an image, such as image 100 (e.g., a model/query image), an image recognition search may be facilitated using the plurality of global signatures to search a document image database.

Global Signatures for Large-Scale Image Recognition

Figure 2:
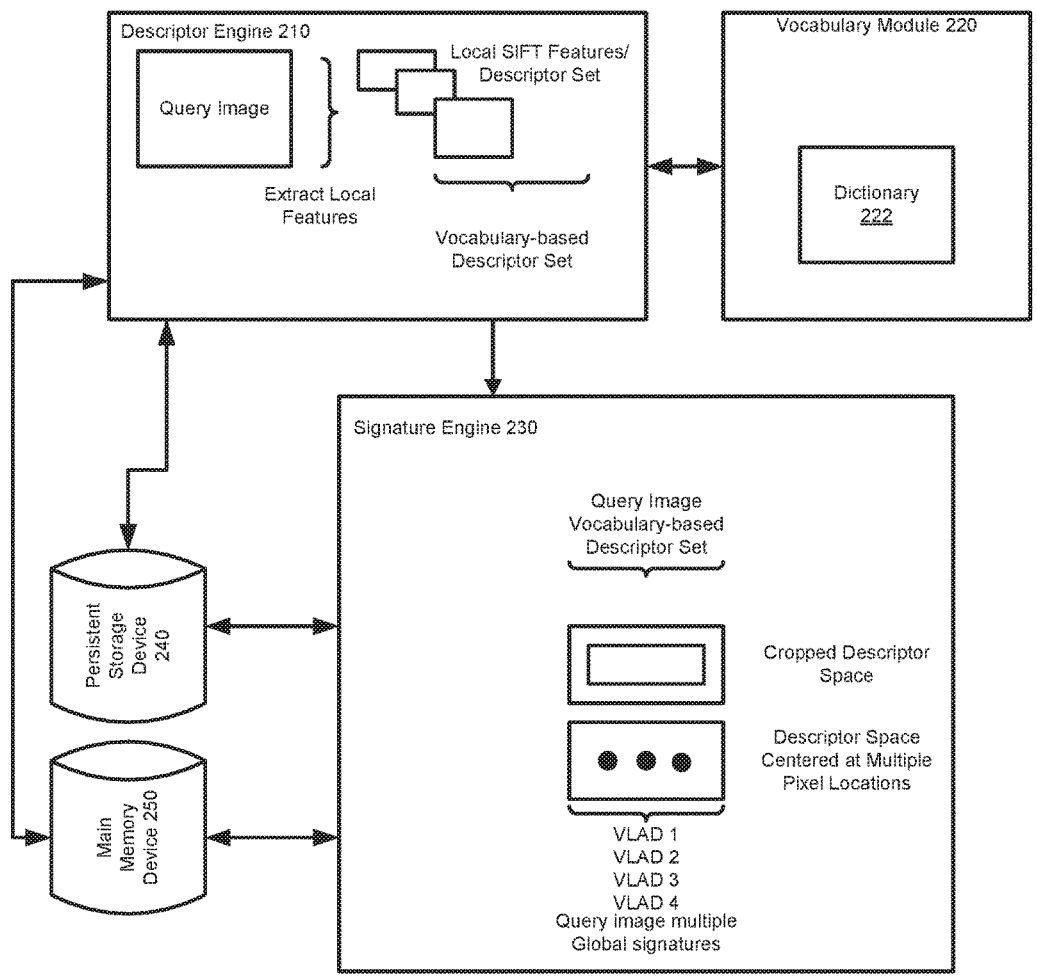
FIG. 2 illustrates a block diagram of a system for generating a plurality of global signatures for an image in accordance with an embodiment.

FIG. 2 illustrates a block diagram of a system for generating a plurality of global signatures for an image in accordance with an embodiment. In block diagram 200, elements for generating global signatures for a query image include a descriptor engine 210, a vocabulary module 220, a signature engine 230, a persistent storage device 240 and a main memory device 250. However, it should be noted that the elements in FIG. 2, and the various functions attributed to each of the elements, while exemplary, are described as such solely for the purposes of ease of understanding. One skilled in the art will appreciate that one or more of the functions ascribed to the various elements may be performed by any one of the other elements, and/or by an element (not shown) configured to perform a combination of the various functions. Therefore, it should be noted that any language directed to descriptor engine 210, a vocabulary module 220, a signature engine 230, a persistent storage device 240 and a main memory device 250 should be read to include any suitable combination of computing devices, including servers, interfaces, systems, databases, agents, peers, engines, controllers, modules, or other types of computing devices operating individually or collectively to perform the functions ascribed to the various elements. Further, one skilled in the art will appreciate that one or more of the functions of the system of FIG. 2 described herein may be performed within the context of a client-server relationship, such as by one or more servers, one or more client devices (e.g., one or more user devices) and/or by a combination of one or more servers and client devices.

In some embodiments, descriptor engine 210 identifies a plurality of local features of an image based on a vocabulary. For example, descriptor engine 210 may extract a plurality of local features from a query image and associate the local features with corresponding local descriptors designed to represent local features. In some embodiments, descriptor engine 210 may be configured to associate local features of the query image with SIFT local descriptors. Alternatively, descriptor engine 210 may be configured to associate local features of the query image with FREAK descriptors, HOG descriptors, SURF descriptors, DAISY descriptors, BRISK descriptors, FAST descriptors, BRIEF descriptors, Harris Corners descriptors, Edges descriptors, GLOH descriptors, EOG descriptors or TILT descriptors.

In an embodiment, descriptor engine 210 is configured to generate a global vocabulary-based descriptor set for the query image. For example, descriptor engine 210 may be coupled to vocabulary module 220 to obtain an associated visual word in a global vocabulary for each of the plurality of local descriptors in the query image. Vocabulary module 220 includes a dictionary 222 that may be used to associate local descriptors with visual words. For example, dictionary 222 may be a VLAD dictionary in which a plurality of visual words are based on descriptors determined from a training sample of model images. Exemplary systems and methods for generating a global vocabulary, such as for a global vocabulary-based descriptor set, are described in U.S. patent application Ser. No. 14/622,621, entitled "Global Visual Vocabulary, Systems and Methods", filed on Feb. 13, 2015, which is incorporated in its entirety by reference herein.

In an embodiment, signature engine 230 is coupled to descriptor engine 210 and configured to obtain the vocabulary-based descriptor set for the query image (i.e., the associated visual words for each of the plurality of local descriptors). Signature engine 230 is then configured to use the descriptor set to generate a plurality global signatures for the query image based on the associated visual words. The plurality of global signatures may be VLAD global signatures. As described in FIG. 1A, some of the plurality of global signatures may be generated using local descriptors corresponding to different cropped versions of the query image (e.g., multiple global signatures centered at a center point and at one or more different off-center pixel locations). The cropped versions of the query image may be determined, for example, in order to focus a VLAD signature around one or more features or objects in the query image. While a typical query image may be centered around an object of interest, oftentimes distinguishing features are located off-center in an image, or only cover a relatively small portion (i.e., less than a majority portion) of an image. Therefore, in order to improve image recognition performance with regard to such features or objects, multiple VLAD signatures may be generated to account for off-center features or objects.

In some embodiments, signature engine 230 is further configured to facilitate an image recognition search comparing the plurality of global signatures with a plurality of document images. For example, query image VLAD signatures stored in main memory device 250 may be used to conduct a global signature-based image recognition search between the query image and a plurality of document images, such as may be stored in main memory device 250 and/or persistent storage device 240. Moreover, in some embodiments signature engine 230 may obtain one or more vocabulary-based descriptor sets for a document image dataset and may generate global signatures (e.g., VLAD signatures) for one or more document images. As such, signature engine 230 may facilitate an image recognition search by generating global signatures for an image dataset of document images as well as for a query image. Signature engine 230 may then store global signatures for the document image dataset in main memory device 250 and/or persistent storage device 240 to facilitate an image recognition search.

Figure 3:
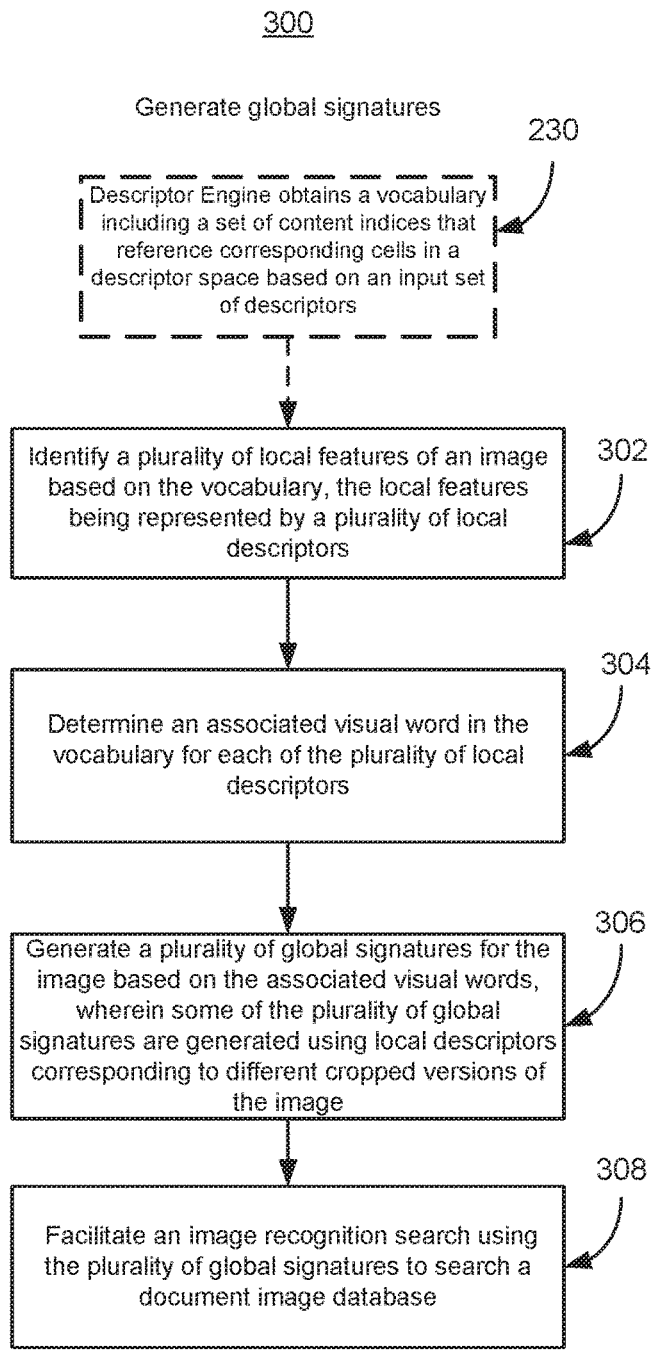
FIG. 3 illustrates a flow diagram of example operations for generating a plurality of global signatures for an image in accordance with an embodiment.

FIG. 3 illustrates a flow diagram of example operations for generating a plurality of global signatures for an image in accordance with an embodiment. In diagram 300, descriptor engine 210 obtains a vocabulary including a set of content indices that reference corresponding cells in a descriptor space based on an input set of descriptors. At step 302, a plurality of local features represented by a plurality of local descriptors are identified for an image, e.g., a query image, based on the vocabulary. In some embodiments, the plurality of local descriptors may be SIFT descriptors. In other embodiments, the plurality of local descriptors may be one of FREAK descriptors, HOG descriptors, SURF descriptors, DAISY descriptors, BRISK descriptors, FAST descriptors, BRIEF descriptors, Harris Corners descriptors, Edges descriptors, GLOH descriptors, EOG descriptors or TILT descriptors. At step 304, an associated visual word in the vocabulary is determined for each of the plurality of local descriptors. For example, a dictionary, such as dictionary 222, may be used to associate local descriptors with visual words. The dictionary may be a VLAD dictionary in which a plurality of visual words are based on descriptors determined from a training sample of model images.

At step 306, signature engine 230 (coupled to descriptor engine 210) generates a plurality of global signatures (e.g., VLAD signatures) for the image based on the associated visual words, wherein some of the plurality of global signatures are generated using local descriptors corresponding to different cropped versions of the image such as, e.g., the cropped versions of an image shown in FIG. 1A. In some embodiments, a one of the plurality of global signatures generated using local descriptors corresponding to a cropped version of the image may be centered at a different pixel location of the image (e.g., at one of pixel locations 112 or 114 of FIG. 1A) with respect to another one of the plurality of global signatures. In some embodiments, one of the plurality of global signatures may be generated using local descriptors corresponding to an uncropped version of the image. The plurality of global signatures will preferably include at least four global signatures, but more or fewer global signatures may be generated. At step 308, signature engine 230 may facilitate an image recognition search using the plurality of global signatures to search a document image database.

The embodiments herein may be useful to address various memory footprint and precision challenges associated with large-scale image recognition systems possibly implemented on one or more web-based servers. Moreover, the entire infrastructure of large-scale image recognition systems, including the main memory and persistent storage devices, servers and user devices, can be made more efficient for processing image recognition queries due to the various embodiments. As described above, global signature-based image recognition may include generating a plurality of global signatures for a query image. For example, generating a global signature can include extracting local descriptors corresponding to local features from a query image. The local descriptors for each feature may then be associated with visual words of a global signature vocabulary (e.g., a VLAD signature vocabulary), and one or more global signatures may be generated for the query image based on the associated visual words. In some embodiments, some of the one or more global signatures are generated using local descriptors corresponding to different cropped versions of the image. Multiple global signatures (e.g., VLAD global signatures) may be generated for query images to improve image recognition accuracy with respect to objects that may be off-center, or that cover relatively small areas of query images or document images. In one embodiment, global signature-based image recognition may further include comparing the one or more query image global signatures with a plurality of document image global signatures.

It should be noted that the global signature-based image recognition systems and methods described herein contemplate large-scale image recognition. For example, a large-scale image recognition system may include one or more document servers, e.g., cloud-based servers, which may offer their services via web-based APIs. In some embodiments, the techniques for generating global signatures may allow one or more of the document servers to contain global signatures corresponding to more than 10 million document images and corresponding document information. For example, a typical server may contain global signatures corresponding to 40 million document images. Moreover, the document servers contemplated by some embodiments may be capable of a search response time that allows for image recognition based on multiple query image global signatures at 5 to 10 frames (images) per second.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computers and interact via a network. The client-server relationship may be defined and controlled by computer programs running on the respective client and server computers.

Figure 4:
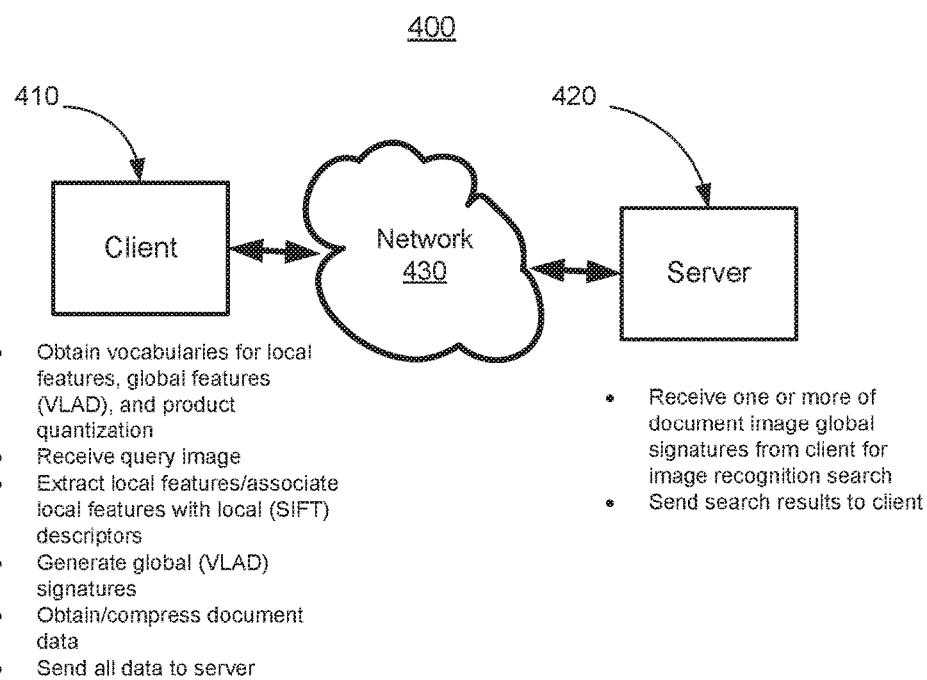
FIG. 4 illustrates a block diagram of an exemplary client-server relationship that can be used for implementing one or more aspects of the various embodiments.

A high-level block diagram of an exemplary client-server relationship that may be used to implement systems, apparatus and methods described herein is illustrated in FIG. 4. Client-server relationship 400 comprises client 410 in communication with server 420 via network 430, and illustrates one possible division of global-signature based image recognition tasks between client 410 and server 420. For example, client 410, in accordance with the various embodiments described above, may obtain vocabularies for local features, global (VLAD) features, and for product quantization. Client 410 may receive a query image, extract local features/associate local features with local (SIFT) descriptors, generate global (VLAD) signatures (e.g., for query and document images) and obtain/compress document data (e.g., reduced quality images) for communication to server 420. Server 420 may, in turn, receive the one or more query and document image global signatures from client 410 for an image recognition search, and may send search results to client 410. One skilled in the art will appreciate that the exemplary client-server relationship illustrated in FIG. 4 is only one of many client-server relationships that are possible for implementing the systems, apparatus, and methods described herein. As such, the client-server relationship illustrated in FIG. 4 should not, in any way, be construed as limiting. Examples of client devices 410 can include cell phones, kiosks, personal data assistants, tablets, toys, vehicles, web cameras, or other types of computer devices.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 1B and 3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
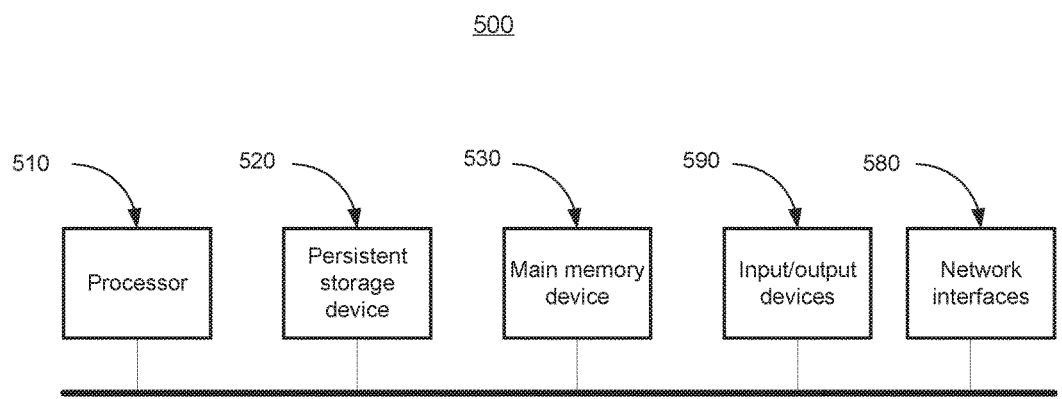
FIG. 5 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 5. Apparatus 500 comprises a processor 510 operatively coupled to a persistent storage device 520 and a main memory device 530. Processor 510 controls the overall operation of apparatus 500 by executing computer program instructions that define such operations. The computer program instructions may be stored in persistent storage device 520, or other computer-readable medium, and loaded into main memory device 530 when execution of the computer program instructions is desired. For example, vocabulary module 220, descriptor engine 210 and signature engine 230 may comprise one or more components of computer 500. Thus, the method steps of FIGS. 1B and 3 can be defined by the computer program instructions stored in main memory device 530 and/or persistent storage device 520 and controlled by processor 510 executing the computer program instructions. For example, the computer program instructions can be implemented as computer executable code programmed by one skilled in the art to perform an algorithm defined by the method steps of FIGS. 1B and 3. Accordingly, by executing the computer program instructions, the processor 510 executes an algorithm defined by the method steps of FIGS. 1B and 3. Apparatus 500 also includes one or more network interfaces 580 for communicating with other devices via a network. Apparatus 500 may also include one or more input/output devices 590 that enable user interaction with apparatus 500 (e.g., display, keyboard, mouse, speakers, buttons, etc.).

Processor 510 may include both general and special purpose microprocessors, and may be the sole processor or one of multiple processors of apparatus 500. Processor 510 may comprise one or more central processing units (CPUs), for example. Processor 510, persistent storage device 520, and/or main memory device 530 may include, be supplemented by, or incorporated in, one or more application-specific integrated circuits (ASICs) and/or one or more field programmable gate arrays (FPGAs).

Persistent storage device 520 and main memory device 530 each comprise a tangible non-transitory computer readable storage medium. Persistent storage device 520, and main memory device 530, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 590 may include peripherals, such as a printer, scanner, display screen, etc. For example, input/output devices 590 may include a display device such as a cathode ray tube (CRT), plasma or liquid crystal display (LCD) monitor for displaying information (e.g., an image recognition search result) to a user, a keyboard, and a pointing device such as a mouse or a trackball by which the user can provide input to apparatus 500.

Any or all of the systems and apparatus discussed herein, including vocabulary module 220, descriptor engine 210 and signature engine 230 may be performed by, and/or incorporated in, an apparatus such as apparatus 500.

One skilled in the art will recognize that an implementation of an actual computer or computer system may have other structures and may contain other components as well, and that FIG. 5 is a high level representation of some of the components of such a computer for illustrative purposes.

The foregoing specification is to be understood as being in every respect illustrative and exemplary, but not restrictive, and the scope of the invention disclosed herein is not to be determined from the specification, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

I claim:

1. A method for large-scale image recognition, comprising:
    obtaining, by a descriptor engine, a vocabulary including a set of content indices that reference corresponding cells in a descriptor space based on an input set of descriptors;
    identifying, by the descriptor engine, a plurality of local features of an image based on the vocabulary, the local features being represented by a plurality of local descriptors;
    determining, by the descriptor engine, an associated visual word in the vocabulary for each one of the plurality of local descriptors;
    generating, by a signature engine coupled to the descriptor engine, a plurality of global signatures for the image based on the associated visual words, wherein some of the plurality of global signatures are generated using local descriptors corresponding to different cropped versions of the image, two or more of the different cropped versions of the image being centered at a same pixel location of the image; and facilitating, by the signature engine, an image recognition search using the plurality of global signatures to search a document image dataset.

2. The method of claim 1, wherein the image is associated with an image dataset comprising a plurality of images.

3. The method of claim 2, wherein the image dataset comprises at least 10 million images.

4. The method of claim 1, further comprising:
dividing the image into k cluster centers; and
assigning each one of the plurality of local descriptors to a closest one of the k cluster centers.

5. The method of claim 4, wherein k equals 64 or 256.

6. The method of claim 4, further comprising, for each one of the k cluster centers, vector quantizing the local descriptors by recording residuals between vectors of each one of the local descriptors and the cluster centers to which the local descriptors are assigned.

7. The method of claim 6, further comprising concatenating sums of the residuals for each one of the k cluster centers to generate a global signature.

8. The method of claim 7, wherein the global signature is a k*128 dimensional vector of locally aggregated descriptors (VLAD) global signature.

9. The method of claim 1, further comprising compressing one or more of the plurality of global signatures.

10. The method of claim 9, wherein the one or more of the plurality of global signatures is compressed using a principal components analysis (PCA) projection matrix.

11. The method of claim 10, wherein the PCA projection matrix reduces a number of dimensions of the one or more of the plurality of global signatures by a factor of 100 or more.

12. The method of claim 1, wherein the image recognition search is for an object that is located at an off-center location within the image.

13. The method of claim 1, wherein the image recognition search is for an object that covers less than a majority portion of the image.

14. The method of claim 1, wherein the different cropped versions of the image are centered at two or more pixel locations of the image.

15. The method of claim 1, wherein a one of the plurality of global signatures generated using local descriptors corresponding to a cropped version of the image is centered at a different pixel location of the image with respect to another one of the plurality of global signatures.

16. The method of claim 1, wherein one of the plurality of global signatures is generated using local descriptors corresponding to an uncropped version of the image.

17. The method of claim 1, wherein the image is a query image.

18. The method of claim 1, wherein the plurality of global signatures includes at least four global signatures.

19. The method of claim 1, wherein the plurality of local descriptors are one of scale-invariant feature transform (SIFT) descriptors, Fast Retina Keypoint (FREAK) descriptors, Histograms of Oriented Gradient (HOG) descriptors, Speeded Up Robust Features (SURF) descriptors, DAISY descriptors, Binary Robust Invariant Scalable Keypoints (BRISK) descriptors, FAST descriptors, Binary Robust Independent Elementary Features (BRIEF) descriptors, Harris Corners descriptors, Edges descriptors, Gradient Location and Orientation Histogram (GLOH) descriptors, Electrooculography (EOG) descriptors or Transform Invariant Low-rank Textures (TILT) descriptors.

20. The method of claim 1, wherein a dictionary is used to determine the associated visual word in the vocabulary with each of the plurality of local descriptors.

21. The method of claim 20, wherein the dictionary comprises a VLAD dictionary in which a plurality of visual words are based on descriptors determined from a training sample of model images.

22. The method of claim 1, wherein the same pixel location corresponds to a center point of the image.

23. The method of claim 1, further comprising selecting at least one additional pixel location of the image; and
generating, by the signature engine, one or more of the plurality of global signatures for the image using local descriptors corresponding to cropped versions of the image centered at the at least one additional pixel location.

24. The method of claim 1, wherein the plurality of global signatures includes at least one of a VLAD signature, a GIST signature or a Deep Learning signature.

25. The method of claim 1, wherein a distance measurement between global signatures representing images containing an object in common is less than a distance measurement between global signatures representing images that do not contain an object in common.

26. The method of claim 1, wherein the document image dataset comprises global signatures corresponding to each of a plurality of document images.

27. The method of claim 1, wherein the image is a digital representation of at least one of the following: a vehicle, a face, a purchasable product, a printed media item, a vending machine, an appliance, a plant, a sign, biological material, a medical patient and a game component.

28. A system for large-scale image recognition, comprising:
a processor;
a main memory device;
a persistent storage device;
a descriptor engine executable on the processor according to software instructions stored in one of the main memory device and the persistent storage device and configured to:
obtain a vocabulary including a set of content indices that reference corresponding cells in a descriptor space based on an input set of descriptors;
identify a plurality of local features of an image based on the vocabulary, the local features being represented by a plurality of local descriptors; and
determine an associated visual word in the vocabulary for each one of the plurality of local descriptors; and
a signature engine, coupled to the descriptor engine, executable on the processor according to software instructions stored in one of the main memory device and the persistent storage device and configured to:
generate a plurality of global signatures for the image based on the associated visual words, wherein some of the plurality of global signatures are generated using local descriptors corresponding to different cropped versions of the image, two or more of the different cropped versions of the image being centered at a same pixel location of the image; and
facilitate an image recognition search using the plurality of global signatures to search a document image dataset.

29. A computer program product embedded in a non-transitory computer readable medium comprising instructions executable by a computer processor for large-scale image recognition, which, when executed by a processor, cause the processor to perform one or more steps comprising:

obtaining a vocabulary including a set of content indices that reference corresponding cells in a descriptor space based on an input set of descriptors;

identifying a plurality of local features of an image based on the vocabulary, the local features being represented by a plurality of local descriptors;

determining an associated visual word in the vocabulary for each one of the plurality of local descriptors;

generating a plurality of global signatures for the image based on the associated visual words, wherein some of the plurality of global signatures are generated using local descriptors corresponding to different cropped versions of the image, two or more of the different cropped versions of the image being centered at a same pixel location of the image; and facilitating an image recognition search using the plurality of global signatures to search a document image dataset.

30. A system for large-scale image recognition, comprising:

means for obtaining a vocabulary including a set of content indices that reference corresponding cells in a descriptor space based on an input set of descriptors;

means for identifying a plurality of local features of an image based on the vocabulary, the local features being represented by a plurality of local descriptors;

means for determining an associated visual word in the vocabulary for each one of the plurality of local descriptors;

means for generating a plurality of global signatures for the image based on the associated visual words, wherein some of the plurality of global signatures are generated using local descriptors corresponding to different cropped versions of the image, two or more of the different cropped versions of the image being centered at a same pixel location of the image; and means for facilitating an image recognition search using the plurality of global signatures to search a document image dataset.

\* \* \* \* \*